United States Patent [19]

Rottman et al.

[11] Patent Number: 5,082,779

[45] Date of Patent: Jan. 21, 1992

[54] METHOD OF DIRECTING TRANSGENIC EXPRESSION IN ANIMALS USING A PROLACTIN PROMOTER

[75] Inventors: Fritz Rottman, Pepper Pike; Sherron Helms, University Hghts., both of Ohio

[73] Assignee: Edison Animal Biotechnology Center/Ohio University, Athens, Ohio

[21] Appl. No.: 82,243

[22] Filed: Aug. 6, 1987

[51] Int. Cl.$^5$ .................... C12N 15/00; C12P 21/00
[52] U.S. Cl. ..................... 435/172.3; 435/69.1; 800/2; 800/DIG. 1; 935/11; 935/13
[58] Field of Search ............. 435/68, 172.3, 240.2, 435/69.1, 172.3; 800/1, 2, DIG. 1; 935/6, 36, 53, 63

[56] References Cited

U.S. PATENT DOCUMENTS 4,579,821 4/1986 Palmiter et al. ................. 435/68
4,675,297 6/1987 Baxter et al. ................... 435/320
4,725,549 2/1988 Cooke et al. .

OTHER PUBLICATIONS

Low et al., Cell 41, pp. 211-219 (1985).
Camper et al., Journal of Biological Chemistry 260(2), pp. 12246-12251 (1985).
Nelson et al., Nature 322, pp. 557-562 (1986).
Camper et al., DNA 3(3), pp. 237-249 (1984).
Van Brunt, Bio Technology 6(10); 1149, 1151, 1152, 1154 (1988).
Wilmut, New Scientist, 7 Jul. 1988, pp. 56-59.
Slabaugh et al., Endocrinology 110(5):1489-1497 (1982).
Hoeffler et al., Endocrinology 117(1):187-195 (1985).
Salter, et al., Transgenic Chickens:Insertion of Retroviral Genes into the Chicken Germ Line Virology, 157:236-240 (1987).
Zuoyan, et al., Biological Effects of Human Growth Hormone Gene Microinjected into the Fertilized Eggs of Loach, Kexye Tongbau 31:988-990 (1986).
MacLean, et al., Introduction of Novel Genes into Fish, Bio/Technology 5:257-261 (1987).
Rusconi, et al., Transformation of Frog Embryos with a Rabbit $\beta$-globin Gene, Proc. Natl. Acad. Sci. 78:5051-5055 (1981).
Kawade et al., Biol. Interferon Syst., Proc. ISIR-INO Meet., Interferon Syst., 305-311 (1986), Transgenic Mice Carrying Exogenous Mouse Interferon Genes.
Palmiter, R. and Brinster, R., Ann. Rev. Genet. 20:465-99 (1986), Germ-Line Transformation of Mice.
Khillan et al., Proc. Natl. Acad. Sci. 83:725-29 (Feb. 1986), Developmental and Tissue-Specific Expression Directed by the Alpha$_2$ Type I Collagen Promoter . . .
Overbeek et al., Proc. Natl. Acad. Sci. 82:7815-19 (Dec. 1985), Lens-Specific Expression and Developmental Regulation of the Bacterial Chloramphenicol . .

Primary Examiner—Elizabeth C. Weimar
Assistant Examiner—Jasemine C. Chambers

[57] ABSTRACT

A method of expressing a non-prolactin gene in a transgenic animal, said expression occurring essentially only after birth and essentially only in the pituitary cells of said animal, which comprises (a) operably linking said gene to a prolactin promoter to form a transcriptional unit, and (b) introducing said unit into one or more cells of said animal.

9 Claims, No Drawings

METHOD OF DIRECTING TRANSGENIC EXPRESSION IN ANIMALS USING A PROLACTIN PROMOTER

BACKGROUND OF THE INVENTION

1. Field of the Invention

This invention relates to the use of the bovine prolactin promoter to control the expression of heterologous genes in transgenic animals or in cell or tissue culture.

2. Information Disclosure Statement

Prolactin is a hormone secreted by the anterior pituitary. Its biological activities include maintenance of lactation after birth and osmoregulation. Prolactin is required for spermatogenesis in rodents, but its role in that process in humans is unclear. Prolactin is produced by a wide variety of animals, including mammals such as humans, monkeys, cows, pigs, sheep, and rats, and other vertebrates such as fish and birds.

The genes encoding several animal prolactins have been sequenced. Cooke, et al., J. Biol. Chem., 256(8): 4007 (1981) (human); Cooke, et al., J. Biol Chem., 255(13): 6502 (1980)(rat); Nilson et al., Nucleic Acids Res., 8(7): 1561 (1980) (bovine); Kuwana, EP Appl 201,882 (Nov. 20, 1986)(fish).

In particular, the 5' flanking region (promoter) of the bovine prolactin gene, has been characterized. Camper et al., DNA, 3:237-249 (1984); Camper, et al., J. Biol. Chem., 260: 12246-51 (1985); Nilson, et al., Nucl. Acids Res., 8: 1561-73 (1980) ; Sasavage, et al., J. Biol. Chem., 257: 678-81 (1982). A region of high homology among the rat, human and bovine promoters has been noted, Camper et al. (1985). Other homologies are noted in Rottman, et al., in MOLECULAR AND CELLULAR ASPECTS REPRODUCTION 281-299 (Dhindsa and Bahl, eds., 1986).

Expression of the prolactin gene is regulated by many factors, including epidermal growth factor (EGF), thyrotropin releasing hormone (TRH), glucocorticoids, vasoactive intestinal polypeptide, cAMP, ergot alkaloids, dopamine, estrogen, and calcium. See, e.g., Dannies, Ch. 7, "Prolactin", in Handbook of Neurochemistry, Vol. 8, pp. 159–174 (1985). Camper et al. (1985) established that the DNA sequences necessary for regulation by EGF, TRH and dexamethasone lie within the 250 nucleotides immediately flanking the 5' end of the structural gene.

The bovine prolactin (bPRL) promoter (1 Kb fragment) has been fused to a "promoterless" chloramphenicol acetyltransferase (CAT) gene. Camper et al. (1985). Transcription of the CAT gene driven by the bPRL promoter was observed in GH$_3$ cells (a rat pituitary tumor cell line), but not in COS-1 (monkey kidney) or HeLa cells. Transcription was stimulated by EGF and TRH, and inhibited by dexamethasone, a synthetic glucocorticoid hormone. See also Sakai, et al., Abstract, "The Glucocorticoid Receptor Mediates Repression of Transcriptional Enchancers from the Bovine Prolactin Gene," in Steroid Hormone Action, UCLA Winter Symposium (January 1987).

Similarly, Nelson, et al., Nature, 322:557 (1986) reports the coupling of the rat prolactin promoter to a heterologous gene, and the expression of the hybrid gene in tissue culture.

Palmiter and Brinster, Ann. Rev. Genetics, 20: 465–499 (1986) review experiments with gene transfer into the germ-line cells of mice and with gene expression in transgenic mice. Table 4 refers to expression of a "prolactin/SV40 early region" transgene in pituitary (lactotroph) cells of transgenic mice. The researcher (Rosenfeld) apparently observed tumorigenesis in the lactotroph cells.

No admission is made that any of the foregoing references constitute prior art, that work described in the publications of others was in fact performed as described, or that the publication dates given in the publications are exact. Applicants do not necessarily concur with the opinions expressed in the references.

SUMMARY OF THE INVENTION

We have used the bovine prolactin promoter to control the expression of non-prolactin genes in transgenic animals. The prolactin promoter has several advantages which commend its use in the genetic engineering of higher animals:

Tissue Specific Expression: The prolactin gene is expressed primarily in the lactotrophs of the anterior pituitary, and at very low levels in the placenta, but not elsewhere. Demonstration of tissue-specific expression from a prolactin sequence would allow study of the minimum requirements for tissue-specific expression and contribute to the understanding of the capacity of eukaryotic differentiated cells to selectively express specific genes. By limiting the range of expression, we should be able to express genes (such as oncogenes) that could be detrimental to animal development if expressed at multiple sites.

While other tissue-specific expression systems have been constructed (e.g., using the rat elastase to direct expression to the pancreas, or of the mouse crystallin promoter to limit expression to the lens), the pituitary-specific prolactin promoter could be unique because expression should occur in only a subset of pituitary cells (lactotrophs).

Development Specific Expression: The prolactin gene is expressed at very low levels during early fetal life. In cattle, there is a tenfold increase in pituitary prolactin mRNA from midgestation to parturition, and another sixteen fold increase from neonate to adult. Similarly, prolactin is not detected in prenatal or neonatal (0–4 day old mice), but by day 20 is increased tenfold over the levels at day 8. Development-specific expression is advantageous because it will allow us to determine the effects of the expression of other genes at "inappropriate" or altered times in the development of an animal. For example, the expression of a given oncogene during fetal life might be expected to give a result different from expression in an adult. Thus, the prolactin promoter, containing the development-responsive regulatory domains, may be useful in controlling the expression of non-prolactin genes.

Hormonal/Humoral Regulation: The prolactin promoter is induced by estrogen, TRH, EGF, phorbol and cAMP, and inhibited by glucocorticoids, thyroid hormone, vitamin D, dopamine, and ergot alkaloids. The fact that there are multiple regulatory elements provides an opportunity to study concerted regulation by different effectors. Also, not all these compounds can be used in an intact animal and often a regulatory molecule will have multiple effects in vivo. Thus, the availability of many regulatory compounds could allow selection of the most efficient one to be used in vivo.

Since the prolactin promoter is relatively weak, we have enhanced the transcription rate by associating it with the Rous Sarcoma Virus (RSV) enhancer element.

Tissue specificity remained intact, but regulation by EGF an dexamethasone was blunted.

DETAILED DESCRIPTION OF THE INVENTION

In a preferred embodiment, a functional bovine prolactin promoter is fused to a non-prolactin gene, and the construct is introduced into a mammalian cell, particularly a cell of an animal in an embryonic, fetal or neonatal stage of development.

The prolactin promoter may be obtained by any art-recognized technique, such as preparing complementary DNA from prolactin messenger RNA, direct synthesis of the promoter based on its published sequence (see Camper et al., 1984, incorporated by reference herein), or a combination of techniques. The promoter employed may correspond exactly to the native promoter, or it may differ from that promoter by selected insertions or deletions.

In modifying the native promoter, it is important to retain the desired regulation of expression. We have found that the region from $-983$ to $-248$ (a Bgl II restriction site) is not essential for regulation by EGF and dexamethasone, and indeed, the remaining segment drives the fused gene to a higher transcriptional level than does our original 983 bp promoter. It is also of interest that human, rat and bovine prolactin genes have 89% homology in the $-178$ to $-94$ region of the bovine prolactin sequence. By constructing a series of deletion mutants, we were able to more clearly delineate the regulatory domains.

Deletion mutants of plasmid containing the CAT gene driven by the 983bp bovine prolactin promoter were constructed as follows: The plasmid was linearized at the 5' end of the prolactin sequence and timed Exo III digestion was performed to successively remove bases 5' to 3'. The DNA was "blunt ended", Bam HI linkers added, and the plasmid recirculized. The number of bases of prolactin sequence present was determined by DNA sequencing. Seventy-four pairs of prolactin sequence were found.

This series of prolactin 5' deletions fused to the CAT gene have been used in transfection experiments in GH$_3$, COS-1 and He La cells as previously described. Transcription of the CAT gene driven by the prolactin promoters was detected only in the GH$_3$ cells with all deletions tested. The level of transcription in GH$_3$ cells with all deletions tested. The level of transcription in GH$_3$ cells is similar in all deletions up to $-236$ bp. Sequences containing from $-248$ to $-236$ bp of 5' flanking prolactin sequences resulted in approximately 32% conversion in the CAT assay. There is transcription at approximately 60% of this level with deletion through $-185$. With less than 185 bp of 5' flanking sequences, the transcription level fails to less than 10% of that seen with the $-236$ sequence. The level of CAT activity is suppressed by dexamethasone in all deletions with detectable CAT activity; however, the magnitude of suppression drops in all mutants containing less than 243 bp of prolactin sequence.

While the bovine prolactin promoter is preferred because of the extensive sequence data available, it is possible to use the prolactin promoters of other mammalian genomes.

Since the prolactin promoter is relatively "weak" transcriptionally (compared to RSV, SV40, CMV, etc.), we have also cloned the RSV enchancer fragment into a vector containing 243 bp of the prolactin promoter and the CAT gene. We received RSV CAT from Bruce Howard, NCI. RSV CAT was linearized with Sph I; then Hind III linkers were added at this site. The vector was recircularized and cut with Hind III to remove the 1786 bp fragment containing the RSV promoter. This vector was then cut with Hind III and Bam HI. The larger of the two resulting fragments contained the RSV enhancer and SV 40 sequences. This was linked to the 1875 bp Bam HI fragment of pPRL-243 CAT which contained 243 bp prolactin promoter linked to the CAT gene. The resulting vector, then, contains the RSV enhancer, the prolactin promoter and the CAT gene.

Initially we analyzed expression of this gene (RSV enchancer+prolactin promoter+CAT gene) in tissue culture experiments as described above. The addition of the RSV enchancer increases the expression in GH$_3$ cells 7- to 20-fold over that seen with the prolactin promoter alone. There is a blunting of the regulation by EGF and dexamethasone, however. Without the enhancer present, dexamethasone decreases expression to 20–25% of the initial level. When the enhancer is present, the level of expression with dexamethasone is decreased to approximately 50% of the initial level. EGF increases the expression of prolactin-CAT 6 to 8 fold but when the RSV-prolactin-CAT is tested, EGF increases expression to only 1½ times the initial level. The tissue specificity of this modified promoter appears to remain intact, however, as the range of cells allowing expression of the prolactin promoter continues to be limited when the viral enchancer is added i.e., there is little or no expression in COS-1 or HeLa cells after transfection.

The following DNA molecules have been microinjected into fertilized mouse eggs:

a. pPRL 1 CAT: contains 983 bp of prolactin promoter fused to the chloramphenicol acetyl transferase (CAT) gene with the SV40 polyadenylation signal
b. pPRL Pst CAT: contains 320 bp of prolactin promoter fused to the CAT gene as in a.
c. pPRL 243 CAT: contains 243 bp of prolactin promoter fused to the CAT gene as in a.
d. pRSVe PRL 243 CAT: contains the RSV viral enhancer and 243 bp prolactin promoter fused to the CAT gene as in a.
e. pPRL 1 bGH: contains 983 bp prolactin promoter fused to the bovine growth hormone (bGH) gene with its polyadenylation signal
f. pRSVe PRL 243 bGH: contains the RSV enhancer and 243 bp of the prolactin promoter fused to the bGH gene as in e.

This microinjection technique is described in Wagner and Hoppe WO 82/04443. However, this invention is not limited to nay particular technique of introducing the recombinant DNA molecules into the animal.

Moreover, the prolactin promoter of this invention may be used to drive other genes than CAT or bGH, such as other pituitary hormones (especially growth hormones) and cellular oncogenes c-fos and c-myc.

Resulting mice were screened for the presence of the CAT DNA by dot-blot hybridization of mouse DNA. Total nucleic acids were isolated from a 2–3 cm segment of tail and spotted onto nitrocellulose filters. The filters were hybridized with $^{32}$P-labelled pSVO-CAT DNA. This technique allows the determination of which animals have the DNA of interest and the approximate number of copies per genome (by comparison with appropriate standards). To confirm that the gene of interest is integrated into the germ line and the animal is not mosaic, the offspring are screened in a similar manner to ascertain that the gene is inherited in a Mendelian fashion and in a copy number similar to parents.

Screening for the expression of bGH by transgenic animals (see "e" and "f" above) is preferably performed by an immunoassay of the animals' sera. Our preferred anti-BGH antibody is described in Desrosiers, et al, Mol. Cell. Biol. 5: 2796–2803 (1985 . The tissue(s) of origin of bGH detected in animal sera will be determined by the presence of bGH messenger RNA in the tissue. This message is relatively stable and should be detectable in the tissue(s) producing BGH. Total cellular mRNA is prepared from multiple tissues by standard techniques. This RNA is electrophoresed, transferred to a membrane and "probed" with bGH to determine if growth hormone mRNA is present.

Our studies have confirmed that the heterologous gene is being expressed in mice tissue-specific manner, though at low levels of expression:

a. pPRL 1 CAT Initial tail blots identified 12 animals ("founder") with CAT sequences in the total DNA.
  1 animal died before assay done.
  3 animals appeared to be 'mosaic' (i.e., the CAT DNA was not integrated in the germ line)
  3 animals could not be bred (and, thus, no offspring were available for assay)
  3 animals had no detectable expression
  1 animal (#16) had very low level of expression only in the pituitary, but offspring and siblings did not express.

b. pPRL PST CAT: Four "founders" identified.
  3 were apparent mosaics.
  1 animal (#108) shows a low level expression in pituitary, brain, and adrenal and a lower, near-background level in hear and liver. This pattern of expression has been noted in seven animals of the first and second generation offspring of the founder.

c. pPRL 243 CAT: 44 animals were screened; five were "positive" on tail blot. Of these five, one is mosaic, three have no expression and one has not yet been tested.

d. pSVe PRL 243 CAT: Twenty-four animals were screened: two were "positive" on tail blot. One animal died before assay. Offspring of the remaining animal are currently being tested. The initial two offspring have no detectable CAT activity in any tissue.

e. pPRL 1 bGH: Twenty-six animals have been screened by ELISA. All were negative.

f. pRSVe PRL 243 bGH: Sixty-seven animals have been tested in ELISA. Of these, five had detectable levels of bGH in the serum as noted below:
  #49–0.1 ng/ul
  #79–0.01 ng/ul
  #63–0.025 ng/ul
  #74–0.025 ng/ul
  #32–0.005 ng/ul Certain bovine prolactin promoter/bovine growth hormone fusions were introduced into swine, again by microinjection into fertilized eggs. Several transgenic piglets were thereby obtained, and expression of bovine growth hormone was observed. (The cross-reactivity of porcine growth hormone with our anti-bGH antiserum was 6.9%).

The sequence of the bovine prolactin promoter from −474 to the cap site is given in Camper, et al. (1984), and is incorporated by reference herein.

We claim:

1. A method of producing a mammal capable of expressing a non-prolactin gene said expression occurring essentially only after birth and essentially only in the pituitary cells of said mammal, which comprises (a) operably linking said gene to a developmentally specific prolactin promoter to form a transcriptional unit and (b) introducing said unit into one or more cells of said mammal at the embryonic stage or of an ancestor of said mammal at the embryonic stage.

2. The method of claim 1, wherein the promoter is the bovine promoter.

3. The method of claim 2, wherein the promoter comprises EGF-and dexamethasone-responsive regulatory elements.

4. The method of claim 1, in which expression is essentially limited to the lactotrophic cells of the pituitary.

5. The method of claim 1, in which the gene encodes a pituitary hormone other than prolactin.

6. The method of claim 1, in which the hormone is a growth hormone.

7. The method of claim 1, in which the gene encodes a cellular oncogene.

8. The method of claim 1, said promoter being operably associated with an RSV enhancer which enhances expression of said gene.

9. The method of claim 1 wherein the prolactin promoter is derived from a first species and the mammal is of a second and different species.

* * * * *